US010648978B2

(12) United States Patent
Wang et al.

(10) Patent No.: US 10,648,978 B2
(45) Date of Patent: May 12, 2020

(54) METHODS FOR DETECTING NOVEL AUTOANTIBODIES IN CROHN'S DISEASE

(71) Applicants: ARIZONA BOARD OF REGENTS ON BEHALF OF ARIZONA STATE UNIVERSITY, Scottsdale, AZ (US); MAYO FOUNDATION FOR MEDICAL EDUCATION AND RESEARCH, Rochester, MN (US)

(72) Inventors: Haoyu Wang, New York, NY (US); Ji Qiu, Chandler, AZ (US); Joshua LaBaer, Chandler, AZ (US); Jonathan Leighton, Scottsdale, AZ (US); Shabana Pasha, Scottsdale, AZ (US)

(73) Assignees: Mayo Foundation for Medical Education and Research, Rochester, MN (US); Arizona Board of Regents on behalf of Arizona State University, Scottsdale, AZ (US)

( * ) Notice: Subject to any disclaimer, the term of this patent is extended or adjusted under 35 U.S.C. 154(b) by 85 days.

(21) Appl. No.: 15/892,981

(22) Filed: Feb. 9, 2018

(65) Prior Publication Data

US 2018/0224448 A1    Aug. 9, 2018

Related U.S. Application Data (60) Provisional application No. 62/457,040, filed on Feb. 9, 2017.

(51) Int. Cl.
| | |
|---|---|
| G01N 33/564 | (2006.01) |
| G01N 33/50 | (2006.01) |
| G01N 33/52 | (2006.01) |
| G01N 33/543 | (2006.01) |
| C12N 15/10 | (2006.01) |
| C07K 16/18 | (2006.01) |
| C07K 16/30 | (2006.01) |
| C07K 16/40 | (2006.01) |

(52) U.S. Cl.
CPC ........... *G01N 33/564* (2013.01); *C07K 16/18* (2013.01); *C07K 16/30* (2013.01); *C07K 16/3069* (2013.01); *C07K 16/40* (2013.01); *C12N 15/1065* (2013.01); *G01N 33/5023* (2013.01); *G01N 33/521* (2013.01); *G01N 33/5436* (2013.01); *G01N 33/54353* (2013.01); *G01N 33/54393* (2013.01); *C07K 2317/30* (2013.01); *C12N 2310/3519* (2013.01); *G01N 2800/065* (2013.01)

(58) Field of Classification Search
None
See application file for complete search history.

(56) References Cited

U.S. PATENT DOCUMENTS

| | | |
|---|---|---|
| 9,442,111 B2 | 9/2016 | Lindsay et al. |
| 9,535,070 B2 | 1/2017 | Saul et al. |
| 9,719,144 B2 | 8/2017 | Krajmalnik-Brown et al. |
| 9,857,374 B2 | 1/2018 | Festa et al. |
| 9,938,523 B2 | 4/2018 | Labaer |
| 10,045,990 B2 | 8/2018 | Festa et al. |
| 10,351,842 B2 | 7/2019 | Labaer |
| 2005/0048580 A1 | 3/2005 | Labaer et al. |
| 2005/0260653 A1 | 11/2005 | Labaer et al. |
| 2012/0330001 A1 | 12/2012 | Darzins et al. |
| 2014/0141991 A1 | 5/2014 | Saul et al. |
| 2014/0162902 A1 | 6/2014 | Labaer et al. |
| 2014/0371091 A1 | 12/2014 | Wiktor et al. |
| 2015/0362497 A1 | 12/2015 | Anderson et al. |
| 2016/0041159 A1 | 2/2016 | Labaer et al. |
| 2016/0083793 A1 | 3/2016 | Labaer et al. |
| 2016/0122751 A1 | 5/2016 | Labaer |
| 2016/0195546 A1 | 7/2016 | Labaer et al. |
| 2017/0045515 A1 | 2/2017 | Anderson et al. |
| 2017/0115299 A1 | 4/2017 | Saul et al. |
| 2017/0176423 A1 | 6/2017 | Anderson et al. |
| 2017/0356029 A1 | 12/2017 | Krajmalnik-Brown et al. |
| 2017/0363631 A1 | 12/2017 | Labaer et al. |
| 2018/0067117 A1 | 3/2018 | Labaer et al. |
| 2018/0201923 A1 | 7/2018 | Labaer |
| 2018/0267029 A1 | 9/2018 | Wiktor et al. |
| 2018/0320230 A1 | 11/2018 | Labaer et al. |
| 2019/0004051 A1 | 1/2019 | Labaer et al. |
| 2019/0062728 A1 | 2/2019 | Labaer et al. |
| 2019/0127778 A1 | 5/2019 | Labaer et al. |
| 2019/0144923 A1 | 5/2019 | Krajmalnik-Brown et al. |
| 2019/0162725 A1 | 5/2019 | Magee et al. |

FOREIGN PATENT DOCUMENTS

| | | |
|---|---|---|
| WO | 2011142900 A1 | 11/2011 |
| WO | 2012021887 A2 | 2/2012 |
| WO | 2013019680 A1 | 2/2013 |
| WO | 2013063126 A2 | 5/2013 |
| WO | 2013090364 A1 | 6/2013 |
| WO | 2013176774 A9 | 11/2013 |
| WO | 2014120902 A1 | 8/2014 |
| WO | 2014143954 A2 | 9/2014 |
| WO | 2014145458 A1 | 9/2014 |
| WO | 2015148202 A1 | 10/2015 |

(Continued)

OTHER PUBLICATIONS

&Nbsp;  Budde et al. (Lupus 2016 vol. 25, p. 812-822). (Year: 2016).*

(Continued)

*Primary Examiner* — Changhwa J Cheu
(74) *Attorney, Agent, or Firm* — Fish & Richardson P.C.

(57) ABSTRACT

Identification of autoantibodies associated with Crohn's disease useful in diagnosis and management using an innovative protein array technology, namely nucleic acid programmable protein arrays (NAPPA) and applications relating thereto. Overall, reactivity of IgG autoantibodies was stronger than that of IgA autoantibodies; however, IgA autoantibodies showed greater differential reactivity between cases and controls. Four IgA autoantibodies against SNRPB, PRPH, PTTG1 and SNAI1 were newly identified with sensitivities above 15% at 95% specificity, among which anti-SNRPB-IgA had the highest sensitivity of 24.0%. Autoantibodies associated with specific disease subtypes were also found.

14 Claims, 7 Drawing Sheets

(56) References Cited

FOREIGN PATENT DOCUMENTS

| WO | 2015167678 A1 | 11/2015 |
| --- | --- | --- |
| WO | 2015175755 A1 | 11/2015 |
| WO | 2016094558 A1 | 6/2016 |
| WO | 2016141044 A1 | 9/2016 |
| WO | 2017048709 A1 | 3/2017 |
| WO | 2017075141 A1 | 5/2017 |
| WO | 2017123648 A1 | 7/2017 |
| WO | 2017218677 A2 | 12/2017 |
| WO | 2018013531 A1 | 1/2018 |
| WO | 2018156553 A1 | 8/2018 |
| WO | 2019136169 A1 | 7/2019 |

OTHER PUBLICATIONS

Arthritis Res Ther. 2012 vol. 14 R77 Supplemental Table 1 total 9 pages (Year: 2012).*

Qiu et al. (Methods in Enzymology 2011 vol. 50, p. 151-163 (Year: 2011).*

Ramachandran, N. et al., "Tracking humoral responses using self assembling protein microarrays", Proteomics. Clinical Applications, Oct. 2008, vol. 2, No. 10-11, pp. 1518-1527 <DOI:10.1002/prca.200800034>.

Ramirez, A. et al., "Use of a single-chain antibody library for ovarian cancer biomarker discovery", Molecular Cell Proteomics, Jul. 2010, vol. 9, No. 7, pp. 1449-1460 <DOI:10.1074/mcp.M900496-MCP200>.

Roggenbuck, D. et al., "Autoimmunity in Crohn's disease—a putative stratification factor of the clinical phenotype", Advances in Clinical Chemistry, 2016, vol. 77, pp. 77-101 <DOI:10.1016/bs.acc.2016.06.002>.

Roggenbuck, D. et al., "Identification of GP2, the major zymogen granule membrane glycoprotein, as the autoantigen of pancreatic antibodies in Crohn's disease", Gut, Dec. 2009, vol. 58, No. 12, pp. 1620-1628 <DOI:10.1136/gut.2008.162495>.

Sabery, N. et al., "Use of serologic markers as a screening tool in inflammatory bowel disease compared with elevated erythrocyte sedimentation rate and anemia", Pediatrics, Jan. 2007, vol. 119, No. 1, article e193 (9 pages) <DOI:10.1542/peds.2006-1361>.

Saxon, A. et al., ". A distinct subset of antineutrophil cytoplasmic antibodies is associated with inflammatory bowel disease", Journal of Allergy and Clinical Immunology, Aug. 1990, vol. 86, No. 2, pp. 202-210 <DOI:10.1016/S0091-6749(05)80067-3>.

Scharl, M. et al., "Inflammatory bowel disease pathogenesis: what is new?", Current Opinion in Gastroenterology, Jul. 2012, vol. 28, No. 4, pp. 301-309 <DOI:10.1097/MOG.0b013e328353e61e>.

Schoepfer, A. et al., "Phenotypic associations of Crohn's disease with antibodies to flagellins A4-Fla2 and Fla-X, ASCA, p-ANCA, PAB, and NOD2 mutations in a Swiss Cohort", Inflammatory Bowel Diseases, Sep. 2009, vol. 15, No. 9, pp. 1358-1367 <DOI:10.1002/ibd.20892>.

Seiler, C. et al., "DNASU plasmid and PSI:Biology-Materials repositories: resources to accelerate biological research", Nucleic Acids Research, Jan. 2014 (available online Nov. 2013), vol. 42, No. D1, pp. D1253-D1260 <DOI:10.1093/nar/gkt1060>.

Silverberg, M. et al., "Toward an integrated clinical, molecular and serological classification of inflammatory bowel disease: report of a working party of the 2005 Montreal world congress of gastroenterology", Canadain Journal of Gastroenterology, Sep. 2005, vol. 19, Supplement A, pp. 5-36 <DOI:10.1155/2005/269076>.

Targan, S. et al., "Antibodies to CBir1 flagellin define a unique response that is associated independently with complicated Crohn's disease", Gastroenterology, Jun. 2005, vol. 128, No. 7, pp. 2020-2028 <DOI:10.1053/j.gastro.2005.03.046>.

Vermeire, S. et al., "(Auto)Antibodies in Inflammatory Bowel Diseases", Gastroenterology Clinics of North America, Jun. 2008, vol. 37, No. 2, pp. 429-438 <DOI:10.1016/j.gtc.2008.03.001>.

Vermeulen, N. et al., "Identification of a novel autoantigen in inflammatory bowel disease by protein microarray", Inflammatory Bowel Diseases, Jun. 2011 (available online Oct. 2010), vol. 17, No. 6, pp. 1291-1300 <DOI:10.1002/ibd.21508>.

Wang, H. et al., "Identification of Antibody Against SNRPB, Small Nuclear Ribonucleoprotein-Associated Proteins B and B', as an Autoantibody Marker in Crohn's Disease using an Immunoproteomics Approach", Journal of Crohn's & Colitis, Jul. 2017, vol. 11, No. 7, pp. 848-856 <DOI:10.1093/ecco-jcc/jjx019>.

Wang, J. et al., "Comparative study of autoantibody responses between lung adenocarcinoma and benign pulmonary nodules", Journal of Thoracic Oncology, Mar. 2016, vol. 11, No. 3, pp. 334-345 <DOI:10.1016/j.jtho.2015.11.011>.

Wang, J. et al., "Plasma autoantibodies associated with basal-like breast cancers", Cancer Epidemiology, Biomarkers and Prevention, Sep. 2015, vol. 24, No. 9, pp. 1332-1340 <DOI:10.1158/1055-9965.EPI-15-0047>.

Wiemann, S. et al., "The ORFeome collaboration: a genome-scale human ORF-clone resource", Nature Methods, Mar. 2016, vol. 13, No. 3, pp. 191-192 <DOI:10.1038/nmeth.3776>.

Wright, C. et al., "Detection of multiple autoantibodies in patients with ankylosing spondylitis using nucleic acid programmable protein arrays", Molecular Cell Proteomics, Feb. 2012, vol. 11, No. 2, article M9.00384 (10 pages) <DOI:10.1074/mcp.M9.00384>.

U.S. Appl. No. 16/097,791.

U.S. Appl. No. 16/317,184.

U.S. Appl. No. 16/480,601.

Anderson, K. et al., "Application of protein microarrays for multiplexed detection of antibodies to tumor antigens in breast cancer", Journal of Proteome Research, Feb. 2008, vol. 7, No. 4, pp. 1490-1499 <DOI:10.1021/pr700804c>.

Anderson, K. et al., "Autoantibody signature for the serologic detection of ovarian cancer", Journal of Proteome Research, 2015 (available online Nov. 2014), vol. 14, No. 1, pp. 578-586 <DOI:10.1021/pr500908n>.

Anderson, K. et al., "Protein microarray signature of autoantibody biomarkers for the early detection of breast cancer", Journal of Proteome Research, 2011 (available online Oct. 2010), vol. 10, No. 1, pp. 85-96 <DOI:10.1021/pr100686b>.

Angenendt, P. et al., "Cell-Free Protein Expression and Functional Assay in Nanowell Chip Format", Analytic Chemistry, Feb. 2004, vol. 76, No. 7, pp. 1844-1849 <DOI:10.1021/ac035114i>.

Ashorn, S. et al., "Serological responses to microbial antigens in celiac disease patients during a gluten-free diet", Journal of Clinical Immunology, Mar. 2009 (available online Nov. 2008), vol. 29, No. 2, pp. 190-195 <DOI:10.1007/s10875-008-9255-7>.

Benor, S. et al., "Shortcomings of the inflammatory bowel disease Serology 7 panel", Pediatrics, Jun. 2010, vol. 125, No. 6, pp. 1230-1236 <DOI:10.1542/peds.2009-1936>.

Bian, X. et al., "Immunoproteomic profiling of antiviral antibodies in new-onset type 1 diabetes using protein arrays", Diabetes, Jan. 2016 (available online Oct. 2015), vol. 65, No. 1, pp. 285-296 <DOI:10.2337/db15-0179>.

Bogdanos, D. et al., "Diagnostic value, clinical utility and pathogenic significance of reactivity to the molecular targets of Crohn's disease specific-pancreatic autoantibodies", Autoimmunity Reviews, Dec. 2011, vol. 11, No. 2, pp. 143-148 <D01:10.1016/j.autrev.2011.09.004>.

Bonneau, J. et al., "Systematic review: New serological markers (anti-glycan, anti-GP2, anti-GM-CSF Ab) in the prediction of IBD patient outcomes", Autoimmunity Reviews, Mar. 2015, vol. 14, No. 3, pp. 231-245 <DOI:10.1016/j.autrev.2014.11.004>.

Bossuyt, X., "Serologic markers in inflammatory bowel disease", Clinical Chemistry, Jan. 2006, vol. 52, No. 2, pp. 171-181 <DOI:10.1373/clinchem.2005.058560>.

Ceroni, A. et al., "Systematic analysis of the IgG antibody immune response against varicella zoster virus (VZV) ising a self-assembled protein microarray", Molecular Biosystems, Jun. 2010, vol. 6, pp. 1604-1610 <DOI:10.1039/c003798b>.

(56) References Cited

OTHER PUBLICATIONS

Degenhardt, F. et al., "Serologic anti-GP2 antibodies are associated with genetic polymorphisms, fibrostenosis, and need for surgical resection in Crohn's disease", Inflammatory Bowel Diseases, Nov. 2016, vol. 22, No. 11, pp. 2648-2657 <DOI:10.1097/MIB.0000000000000936>.

Duck, L. et al., "Isolation of flagellated bacteria implicated in Crohn's disease", Inflammatory Bowel Diseases, Oct. 2007, vol. 13, No. 10, pp. 1191-1201 <DOI.10.1002/ibd.20237>.

Esters, N. et al., "Serological markers for prediction of response to anti-tumor necrosis factor treatment in Crohn's disease", The American Journal of Gastroenterology, Jun. 2002, vol. 97, No. 6, pp. 1458-1462 <DOI:10.1016/S0002-9270(02)04045-5>.

Folwaczny, C. et al., "Antineutrophil and pancreatic autoantibodies in first-degree relatives of patients with inflammatory bowel disease", Scandinavian Journal of Gastroenterology, 1998, vol. 33, No. 5, pp. 523-528 <DOI:10.1080/00365529850172106>.

Folwaczny, C. et al., "Goblet cell autoantibodies in patients with inflammatory bowel disease and their first-degree relatives", Gastroenterology, Jul. 1997, vol. 113, No. 1, pp. 101-106 <DOI:10.1016/S0016-5085(97)70085-4>.

Gibson, D. et al., "Circulating and synovial antibody profiling of juvenile arthritis patients by nucleic acid programmable protein arrays", Arthritis Research and Therapy, Apr. 2012, vol. 14, No. 2, article R77 (12 pages) <DOI:10.1186/ar3800>.

Gupta, N. et al., "Risk factors for initial surgery in pediatric patients with Crohn's disease", Gastroenterology, Apr. 2006, vol. 130, No. 4, pp. 1069-1077 <DOI:10.1053/j.gastro.2006.02.003>.

Herszényi, L. et al., "The role of autoantibodies in inflammatory bowel disease", Digestive Diseases, 2012, vol. 30, pp. 201-207 <DOI:10.1159/000336702>.

Holstein, A. et al., ". Autoantibody profiles in microscopic colitis", Gastroenterology, Jun. 2006, vol. 21, pp. 1016-1020 <DOI:10.1111/j.1440-1746.2005.04027.x>.

Iltanen, S. et al., "Elevated serum anti-I2 and anti-OmpW antibody levels in children with IBD", Inflammatory Bowel Diseases, May 2006, vol. 12, No. 5, pp. 389-394 <DOI:10.1097/01.MIB.0000218765.84087.42>.

Karthikeyan, K. et al., "A contra capture protein array platform for studying post-translationally modified (PTM) auto-antigenomes", Molecular & Cellular Proteomics, Jul. 2016, vol. 15, No. 7, pp. 2324-2337 <DOI:10.1074/mcp.M115.057661>.

Khoo, U. et al., ". Antibodies to colonic epithelial cells from the serum and colonic mucosal washings in ulcerative colitis", Gut, Jul. 1995, vol. 37, No. 1, pp. 63-70 <DOI:10.1136/gut.37.1.63>.

Kinpara, T. et al., "A picoliter chamber array for cell-free protein synthesis", Journal of Biochemistry, Aug. 2004, vol. 136, No. 2, pp. 149-154 <DOI:10.1093/jb/mvh102>.

Kohoutova, D. et al., "Anti-Outer membrane protein C and anti-glycoprotein 2 antibodies in inflammatory bowel disease and their association with complicated forms of Crohn's disease", BMC Gastroenterology, Dec. 2014, vol. 14, No. 190 (7 pages) <DOI:10.1186/s12876-014-0190-1>.

Komorowski, L. et al., "Autoantibodies against exocrine pancreas in Crohn's disease are directed against two antigens: the glycoproteins CUZD1 and GP2", Journal of Crohn's and Colitis, Nov. 2013, vol. 7, No. 10, pp. 780-790 <DOI:10.1016/j.crohns.2012.10.011>.

Koutroubakis, I. et al., "Anti-*Saccharomyces cerevisiae* mannan antibodies and antineutrophil cytoplasmic autoantibodies in Greek patients with inflammatory bowel disease", American Journal of Gastroenterology, Feb. 2001, vol. 96, No. 2, pp. 449-454 <DOI:10.1111/j.1572-0241.2001.03524.x>.

Koutroubakis, I., "Unraveling the mechanisms of thrombosis in inflammatory bowel disease", American Journal of Gastroenterology, May 2001, vol. 96, No. 5, pp. 1325-1327 <DOI:10.1111/j.1572-0241.2001.03846.x>.

Kovacs, M. et al., "Pancreatic autoantibodies and autoantibodies against goblet cells in pediatric patients with nflammatory bowel disease", Journal of Pediatric Gastroenterology and Nutrition, Oct. 2012, vol. 55, No. 4, pp. 429-435 <DOI:10.1097/MPG.0b013e318256b516>.

Kuna, A., "Serological markers of inflammatory bowel disease", Biochemia Medica, Feb. 2013, vol. 23, No. 1, pp. 28-42 <DOI:1011613/BM.2013.006>.

Litvak, D. et al., "Endogenous immune response to early- and intermediate-stage melanoma is correlated with outcomes and is independent of locoregional relapse and standard prognostic factors", Journal of the American College of Surgeons, Jan. 2004, vol. 198, No. 1, pp. 27-35 <DOI:10.1016/j.jamcollsurg.2003.08.012>.

Lodes, M. et al., "Bacterial flagellin is a dominant antigen in Crohn disease", Journal of Clinical Investigation, May 2004, vol. 113, No. 9, pp. 1296-1306 <DOI:10.1172/JCI20295>.

Los, G. et al., "HaloTag: A Novel Protein Labeling Technology for Cell Imaging and Protein Analysis", Chemical Biology, Jun. 2008, vol. 3, No. 6, pp. 373-382 <DOI:10.1021/cb800025k>.

Maloy, K. et al., "Intestinal homeostasis and its breakdown in inflammatory bowel disease", Nature, Jun. 2011, vol. 474, pp. 298-306 <DOI:10.1038/nature10208>.

Michaels, M. et al., "Pancreatic autoantibodies against CUZD1 and GP2 are associated with distinct clinical phenotypes of Crohn's disease", Inflammatory Bowel Diseases, Dec. 2015, vol. 21, No. 12, pp. 2864-2872 <DOI:10.1097/MIB.0000000000000564>.

Miersch, S. et al., "Serological autoantibody profiling of type 1 diabetes by protein arrays", Journal of Proteomics, Dec. 2013, vol. 94, pp. 486-496 <DOI:10.1016/j.jprot.2013.10.018>.

Montor, W. et al., "Genome-Wide Study of Pseudomonas aeruginosa Outer Membrane Protein Immunogenicity Using Self-Assembling Protein Microarrays", Infection and Immunity, Nov. 2009, vol. 77, No. 11, pp. 4877-4886 <DOI:10.1128/IAI.00698-09>.

Papp, M. et al., "Rediscovery of the anti-pancreatic antibodies and evaluation of their prognostic value in a prospective clinical cohort of Crohn's patients: the importance of specific target antigens [GP2and CUZD1]", Journal of Crohn's & Colitis, Aug. 2015, vol. 9, No. 8, pp. 659-668 <DOI:10.1093/ecco-jcc/jjv087>.

Patent Cooperation Treaty, International Searching Authority, International Preliminary Report on Patentability and Written Opinion for PCT/US2012/061702, 10 pages, report dated Apr. 29, 2014.

Patent Cooperation Treaty, International Searching Authority, International Preliminary Report on Patentability and Written Opinion for PCT/US2014/030226, 10 pages, report dated Sep. 15, 2015, opinion dated Aug. 12, 2014.

Patent Cooperation Treaty, International Searching Authority, International Search Report for PCT/US2012/061702, 6 pages, dated Apr. 19, 2013.

Patent Cooperation Treaty, International Searching Authority, International Search Report for PCT/US2014/030226, 2 pages, dated Aug. 12, 2014.

Pavlidis, P. et al., "Diagnostic and clinical significance of Crohn's disease-specific anti-MZGP2 pancreatic antibodies by a novel ELISA", Clinica Chimica Acta, Feb. 2015, vol. 441, pp. 176-181 <DOI:10.1016/j.cca.2014.12.010>.

Pavlidis, P. et al., "Diagnostic and clinical significance of Crohn's disease-specific pancreatic anti-GP2 and anti-CUZD1 antibodies", Clinical Chemistry and Laboratory Medicine, Feb. 2016, vol. 54, No. 2, pp. 249-256 <DOI:10.1515/cclm-2015-0376>.

Plevy, S. et al., "Combined serological, genetic, and inflammatory markers differentiate non-IBD, Crohn's disease, and ulcerative colitis patients", Inflammatory Bowel Diseases, May 2013, vol. 19, No. 6, pp. 1139-1148 <DOI:10.1097/MIB.0b013e318280b19e>.

Podolsky, D., "Inflammatory Bowel Disease", The New England Journal of Medicine, Aug. 2002, vol. 347, pp. 417-429 <DOI:10.1056/NEJMra020831>.

Procaccia, S. et al., "Detection of rheumatoid factors of different isotypes and of circulating immune complexes in patients with inflammatory bowel disease", Bollettino Dell'Isituto Sieroterapico Milanese, Jun. 1990, vol. 69, No. 2, pp. 413-421.

(56) References Cited

OTHER PUBLICATIONS

Quinton, J. et al., "Anti-*Saccharomyces cerevisiae* mannan antibodies combined with antineutrophil cytoplasmic autoantibodies in inflammatory bowel disease: prevalence and diagnostic role", Gut, Jun. 1998, vol. 42, No. 6, pp. 788-791.
Ramachandran, N. et al., "Next-generation high-density self-assembling functional protein arrays", Nature Methods, May 2008, vol. 5, pp. 535-538 <DOI:10.1038/NMETH.1210>.
Ramachandran, N. et al., "Self-assembling protein microarrays", Science, Jul. 2004, vol. 305, No. 5680, pp. 86-90 DOI:10.1126/science.1097639>.

\* cited by examiner

METHODS FOR DETECTING NOVEL AUTOANTIBODIES IN CROHN'S DISEASE

CROSS-REFERENCE TO RELATED APPLICATIONS

This application is based on, claims a priority benefit from, and incorporates herein by reference, U.S. Provisional Patent Application No. 62/457,040, filed Feb. 9, 2017, and entitled "Novel Autoantibodies in Crohn's Disease."

FIELD OF THE INVENTION

This disclosure relates to providing compositions and methods for detecting Crohn's disease.

BACKGROUND

Crohn's disease (CD) is a form of inflammatory bowel disease (IBD) characterized by chronic transmural inflammation and skip lesions that can involve any segment of the gastrointestinal tract. The prevalence of CD has been increasing in recent years. An early accurate detection, determination of prognosis, as well as predicting appropriate therapy are therefore important to curb such increased prevalence.

The pathophysiology of CD is likely related to genetic, environmental and immune system factors. With regard to the immune system, there is evidence to suggest that an overactive intestinal mucosal immune system may be driven at least in part by a reaction to normal/altered luminal flora and autoantigens (AAgs). One manifestation of such a dysregulated immune response is the presence of CD-specific antibodies against gut microorganisms and AAgs. These include antibodies against microbial antigens (e.g., Flagellin, I2, *Saccharomyces cerevisiae* (ASCA)) and autoantibodies (AAbs) such as anti-neutrophil cytoplasmic antibodies (ANCA) and pancreatic antibodies (PAb). To date, the presence of specific antibodies in the serum of patients with CD may help in detection, prognosis, and predicting response to therapy. However, most clinically used serological antibodies were discovered years ago and have a limitation by frequent false positives and an inability to accurately predict disease course. Therefore, there is a need for better diagnostic and prognostic CD markers.

Early studies on AAbs in CD patients used immunofluorescence or whole cell ELISA assays on neutrophils, pancreas, goblet cells and colonic epithelial cells probed with patient sera. Early studies on AAbs in CD patients used immunofluorescence or whole cell ELISA assays on neutrophils, pancreas, goblet cells and colonic epithelial cells probed with patient sera. Although whole-cell signals have been observed in CD for decades, the antigens recognized by these immunofluorescence assays remain largely unknown. This approach has proven to be ineffective, only two AAb targets of PAb have been discovered through mass spectrometry identification of reactive western blot spots. Challenges associated with methods that involve western blot include low throughput, inadequate quantification, and poor reproducibility. While all these technical challenges can be overcome, the level of effort needed to thoroughly analyze even a single sample prevents this approach from use in large clinical sample sets.

Progress in identifying individual autoantigens and autoantibodies in Crohn's disease has been challenging due to limitations of available immunoassays.

SUMMARY

Embodiments of the current disclosure describe methods for detecting an antigen-antibody complex of interest in a disease. The method comprises the steps of disposing a plurality of DNA segments corresponding to different open reading frames of genes on an array, wherein each DNA segment comprises a fusion tag; disposing a plurality of antibodies raised against the fusion tag on the array; translating the plurality of DNA segments to a plurality of polypeptides, wherein each polypeptide comprises the fusion tag and is captured by the antibodies raised against the fusion tag; and incubating the array with the plurality of captured polypeptides with samples collected from subjects having the disease and from healthy subjects to thereby form polypeptide/antibody complexes.

Further, in certain embodiments, the method comprises the steps of providing a plurality of antigens, wherein the antigens are selected from the group consisting of A4-Fla2, flaD, XAGE2, CDC42EP1, PPP1R13L, FOSL1, SNRPB, CCHCR1, LCORL, NUPL1, PRPH, PTTG1, SNAI1, and ORC2L; contacting the plurality of antigens with a sample from a subject containing a plurality of antibodies under conditions suitable to bind to the plurality of antigens to form antigen-antibody complexes; and determining the level or concentrations of said complexes.

BRIEF DESCRIPTION OF THE DRAWINGS

The technology disclosed herein will be better understood from a reading of the following detailed description taken in conjunction with the drawings in which like reference designators are used to designate like elements, and in which:

FIG. 7 illustrates Jitter plots of antibody responses measured by ELISA in cases showing differences in different categories based on patients' clinical parameters: panel (A) Anti-A4-Fla2-IgG measured in patients with different disease behavior B1 (non-stricturing, non-penetrating), B2 (stricturing) and B3 (penetrating); panel (B) Anti-FOSL1-IgA measured in patients with different disease location L1

(ileal), L2 (colonic) and L3 (ileocolonic); panel (C) RF-IgG measured in patients with and without surgery. The black line indicates the median.

DETAILED DESCRIPTION

This technology disclosed herein is described in one or more exemplary embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present technology disclosed herein. Thus, appearances of the phrases "in one embodiment," "in an embodiment," and similar language throughout this specification may, but do not necessarily, all refer to the same embodiment.

The described features, structures, or characteristics of the technology disclosed herein may be combined in any suitable manner in one or more embodiments. In the following description, numerous specific details are recited to provide a thorough understanding of embodiments of the technology disclosed herein. One skilled in the relevant art will recognize, however, that the technology disclosed herein may be practiced without one or more of the specific details, or with other methods, components, materials, and so forth. In other instances, well-known structures, materials, or operations are not shown or described in detail to avoid obscuring aspects of the technology disclosed herein.

The current technology discloses a high-throughput and unbiased method to test and identify different candidate antigens in Crohn's disease. Protein arrays have enabled profiling the antibody immune response in diseases that antibodies can be tested against thousands of proteins in parallel. FAM84A was identified as a novel AAg in IBD using protein arrays. However, conventional ways of making protein arrays require purification of a large number of proteins, making them expensive to produce and difficult to apply to large sample numbers.

Definitions

The term "individual," "subject," or "patient" typically refers to humans, but also to other animals including, e.g., other primates, rodents, canines, felines, equines, ovines, porcines, and the like.

The term "sample" includes any biological specimen obtained from an individual. Suitable samples for use in the present invention include, without limitation, whole blood, plasma, serum, saliva, urine, stool (i.e., feces), tears, and any other bodily fluid, or a tissue sample (i.e., biopsy) such as a small intestine or colon sample, and cellular extracts thereof (e.g., red blood cellular extract). In a preferred embodiment, the sample is a blood, plasma, or serum sample. In a more preferred embodiment, the sample is a serum sample.

The term "capture antibody" is intended to include an immobilized antibody which is specific for (i.e., binds, is bound by, or forms a complex with) one or more analytes of interest in a sample. In particular embodiments, the capture antibody is restrained on a solid support in an array.

The term "sensitivity" means the proportion of patients who are correctly categorized as having disease among those who truly have the disease. Similarly, the term "specificity" means the proportion of patients who are correctly categorized as not having the disease among all patients who truly don't have the disease.

An innovative protein array system termed NAPPA is disclosed here to overcome the above identified problems. NAPPA circumvents many of the limitations of traditional protein microarrays, and entails programming cell free protein expression extracts with cDNAs to express the proteins in situ at the time of the assay without the need for advanced protein purification. A key advantage is that human proteins are produced by human ribosomes and chaperone proteins to increase the efficiency of translation and to encourage natural folding of the proteins. Also, antibodies of both IgG and IgA classes can be probed simultaneously by using corresponding secondary antibodies conjugated with different fluorophores.

Protein arrays were produced displaying 1906 unique human proteins encoded by genes randomly selected from our human gene collections at DNASU (DNASU.org), and 3 known bacterial flagellins as positive controls, A4-Fla2 and Fla-X, and CBir1. We also included 9 bacterial flagellin genes in our collection, flaA, flaB, flaC, flaD, flaE, flaG from *Vibrio cholera*, flgG, flgH, and flgK from *Pseudomonas aeruginosa*. Arrays were quality controlled for protein display. Forty-eight (48) CD patients and 48 age-gender matched healthy controls (Table 1) were profiled for their antibody responses against these 1906 proteins. Antibodies of both IgA and IgG classes were assayed simultaneously using secondary anti-human IgA and anti-human IgG antibodies labeled with different fluorophores. An equal-volume pool of all 48 patient samples and a pool of all 48 controls were tested every experiment day to assure the quality. The correlations between two arrays profiled with the same pooled samples were generally above 0.85. Epstein Barr Nuclear antigen (EBNA) was printed on our arrays as an experimental positive control because more than 90% adults in the United States have been infected by the Epstein Barr virus. Eighty-nine (89) out of the 96 subjects assayed on the arrays showed IgG reactivity against EBNA. Sixty-eight (68) showed much weaker IgA reactivity against EBNA.

Table 1 lists clinical information and characteristics of human subjects.

TABLE 1

Clinical information of the samples

| | Discovery set | | Validation set | |
| --- | --- | --- | --- | --- |
| | CD patients | Healthy controls | CD patients | Healthy controls |
| N (sera) | 48 | 48 | 48 | 48 |
| Gender (male/female) | 21/27 | 21/27 | 21/27 | 21/27 |
| Age, yrs (mean) | 44 ± 17 | 44 ± 17 | 40 ± 16 | 40 ± 16 |
| Age, yrs (range) | 20-77 | 20-77 | 18-74 | 18-74 |
| Age at diagnosis (A1/A2/A3) | 1/24/23 | | 1/29/18 | |
| Location of diseases (L1/L2/L3/L4) | 15/9/24/0 | | 14/8/26/0 | |
| Behavior (B1/B2/B3) | 23/12/13 | | 26/9/13 | |
| Surgery (Y/N) | 18/30 | | 22/26 | |

Age at diagnosis;
A1: 0-16 yrs,
A2: 16-40 yrs,
A3: >40 yrs.
Location of disease;
L1: ileal,
L2: colonic,
L3: ileocolonic,
L4: isolated upper digestive.
Behavior;
B1: non-stricturing, non- penetrating;
B2: stricturing,
B3: penetrating.

Figure 1:
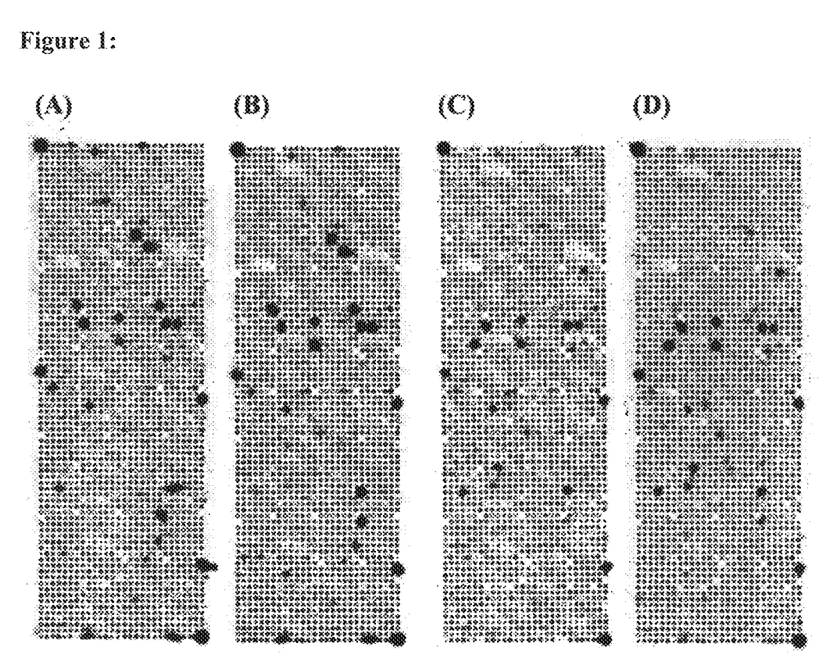
FIG. 1 shows reproducibility of serological profiling on nucleic acid programmable protein arrays (NAPPA). Slide images showed the IgG antibody reactivity toward a pool of 48 samples from CD patients (panels A and B) and a pool of 48 healthy controls (panels C and D) probed on arrays on two different days. Rings indicate strong seroreactivity.

Referring to FIG. 1, a high-throughput study using a protein array screens all proteins simultaneously and is probed with samples from Crohn's disease and controls to identify novel autoantigens against antibodies that are present in samples. Studies that use an immunoproteomics approach to identify CD-specific AAbs of both IgG and IgA classes were conducted. The current NAPPA technology was applied to screen about 1900 human proteins in CD patients and age- and gender-matched controls. Candidate AAbs identified from antibody profiling on protein arrays were first confirmed by Enzyme Linked Immunosorbent Assay (ELISA) and further validated by ELISA in an independent sample set. With the advantage of NAPPA, especially in obtaining thousands of "fresh" proteins with natural folding on the array, characteristics of the humoral immune response were identified, which may have been missed before.

Figure 2:
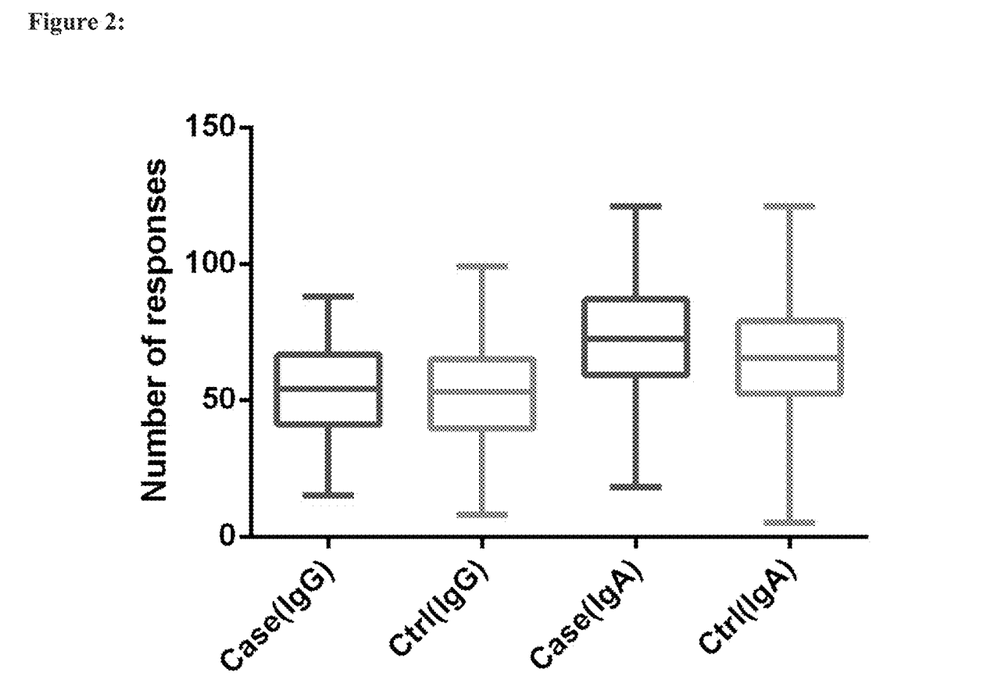
FIG. 2 is a boxplot of number of proteins that showed antibody reactivity for samples in the discovery set on arrays. Number of responses for controls ranged between 8-99 for IgG and 5-121 for IgA. Number of responses for cases ranged between 15-88 for IgG and 18-121 for IgA. The p-values from student's t-test between CD patients and healthy controls are 0.08 for IgA and 0.42 for IgG.
Figure 3:
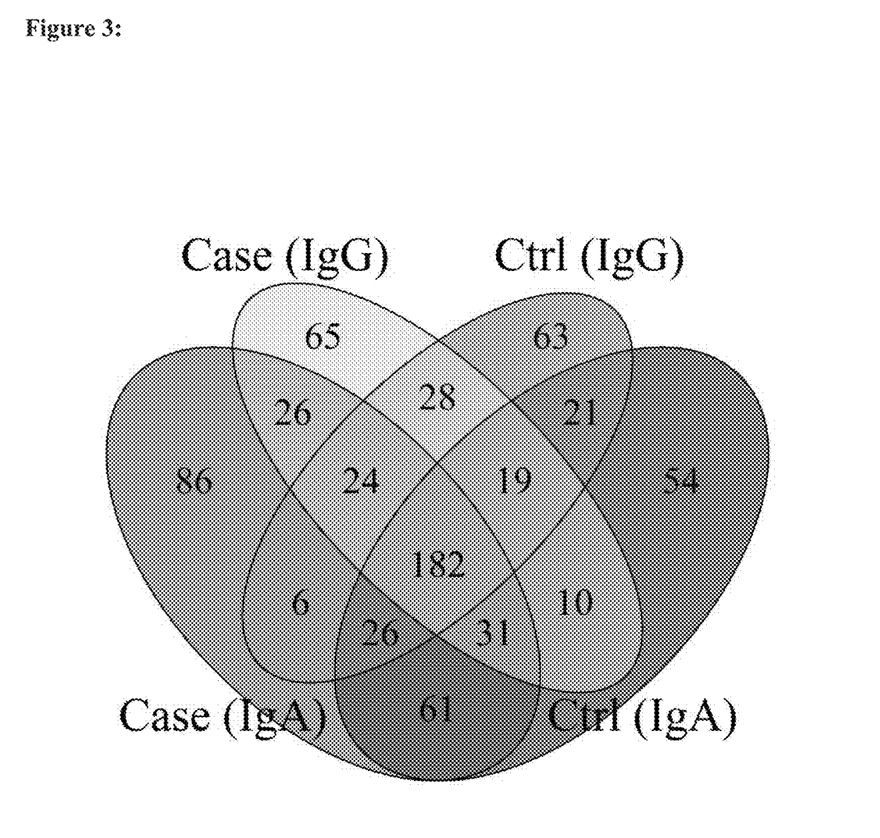
FIG. 3 illustrates a Venn diagram of the number of antigens that reacted with at least two subjects (case or ctrl) on the array for both IgG and IgA antibody classes.

Referring to FIG. 2, the average numbers of human proteins showing IgG antibody reactivity on arrays were 53±19 and 53±20 for cases and controls, respectively. There was no difference between cases and controls (p=0.42) for IgG antibody. However, CD patients showed greater IgA antibody response against proteins on arrays. The average number of proteins showing IgA reactivity for cases (73±22) was greater than that for controls (66±24), although it did not reach statistical significance (p=0.08) (FIG. 2). From the perspective of individual proteins (Table 2), 501 proteins reacted with at least two patients or controls for IgG antibody. When analyzing case and control samples separately, 385 antigens reacted with at least two cases and 369 with at least two controls. There was a big overlap of 253 proteins that reacted with both CD cases and controls (FIG. 3).

TABLE 2

Number and percentage of human proteins which showed positive antibody response on arrays in the discovery sample set with different criteria.

|  | At least two in case or control | At least two in case | At least two in control | Two more in case than in control | Two more in control than in case | At least 15% sensitivity at 95% specificity |
|---|---|---|---|---|---|---|
| IgG | 501 (26.3%) | 385 (20.2%) | 369 (19.4%) | 156 (8.2%) | 146 (7.7%) | 13 (0.7%) |
| IgA | 546 (28.6%) | 442 (23.2%) | 404 (21.2%) | 217 (11.4%) | 135 (7.1%) | 19 1.0%) |

Bacterial flagellin antibodies showed the strongest reactivity and the highest prevalence on arrays. Quantitatively, anti-A4-Fla2-IgG achieved a sensitivity of 46% at 95% specificity among the 48 pairs of samples profiled on arrays, which matched the performance reported in the literature. Anti-A4-Fla2-IgA did not differentiate the cases from control as well as IgG, with a sensitivity of 19% at 95% specificity, which was also comparable to the literature. Other known flagellin antibodies anti-Fla-X-IgG and anti-CBir1-IgG showed very similar performance to anti-A4-Fla2-IgG. Thus, only A4-Fla2 was included for the subsequent experiments.

All novel AAbs discovered on arrays were ranked according to their sensitivity at 95% specificity for IgG and IgA antibodies respectively based on array data. Nine (9) IgG candidate antibodies and 19 IgA candidate antibodies that had at least 10% sensitivity at 95% specificity were selected (Table 3), together with two flagellins (A4-Fla2 and flaD). All these antibodies were verified by ELISA using the discovery sample set listed in Table 1. Three (3) (out of 9) of the IgG candidates and 14 (out of 19) IgA candidates had comparable performance on ELISA and were selected for further validation (Table 3).

TABLE 3

List of candidate antibodies selected by protein array and their sensitivity at 95% specificity based on ELISA result.

| Antibody type | Antigen | Sensitivity (%) at 95% specificity | | |
|---|---|---|---|---|
|  |  | Discovery Set | Validation Set | Entire Set |
| IgG | A4-Fla2 | 50 | 50 | 50 |
|  | flaD | 29 | 17 | 24 |
|  | WWTR1 | 6 |  | N/A |
|  | XAGE2 | 29 | 2 | 14 |
|  | RAD51AP1 | 8 |  | N/A |
|  | STAU1 | 6 |  | N/A |
|  | MAP7 | 8 |  | N/A |
|  | CDC42EP1 | 10 | 10 | 10 |
|  | PML | 10 | 4 | 7 |
|  | FOS | 4 |  | N/A |
|  | KLF4 | 8 |  | N/A |
|  | RF | 21 | 15 | 18 |
| IgA | A4-Fla2 | 21 | 21 | 20 |
|  | PPP1R13L | 25 | 6 | 14 |
|  | FOSL1 | 13 | 23 | 13 |
|  | MACC1 | 4 |  | N/A |
|  | RAD51AP1 | 21 | 0 | 7 |
|  | NUFIP2 | 13 | 23 | 8 |
|  | SNRPB | 25 | 19 | 24 |
|  | ZGPAT | 2 |  | N/A |
|  | CCHCR1 | 15 | 10 | 13 |
|  | LCORL | 10 | 10 | 10 |
|  | NUPL1 | 19 | 4 | 10 |
|  | PAPOLG | 6 |  | N/A |
|  | PRPH | 13 | 15 | 16 |
|  | PTTG1 | 17 | 8 | 16 |
|  | SNAI1 | 10 | 27 | 17 |
|  | C1orf106 | 8 |  | N/A |
|  | FILIP1L | 13 | 4 | 7 |
|  | NEUROD6 | 15 | 2 | 1 |
|  | ORC2L | 15 | 8 | 10 |
|  | STAU1 | 8 |  | N/A |
|  | RF | 33 | 15 | 24 |

Figure 4:
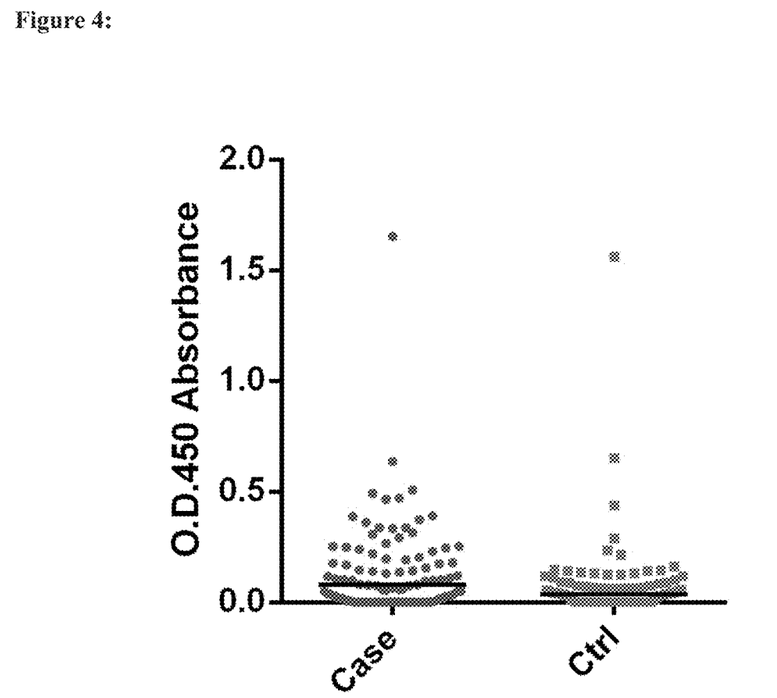
FIG. 4 is a jitter plot of anti-SNRPB-IgA antibody response measured by ELISA in the entire sample set. The black line indicates the median.

We further validated the performance of the 3 IgG and 14 IgA AAgs showing differential antibody responses between cases and controls by ELISA using an independent sample set (validation sample set, Table 1). Validation was also performed on one known flagellin (A4-Fla2) and one novel flagellin (flaD). IgA AAbs against small nuclear ribonucleoprotein-associated proteins B and B' (SNRPB), peripherin (PRPH), securin (PTTG1) and zinc finger protein SNAI1 (SNAI1) had sensitivity above 15% at 95% specificity in the entire sample set (Table 3). Among the newly identified AAb, anti-SNRPB IgA had the highest sensitivity of 24.0% (FIG. 4). We also estimated the anti-SNRPB-IgA titers for all samples by fitting their ELISA absorbance data onto a standard curve generated using serially diluted commercially available human IgA. Significant difference (p=0.01) was also observed between cases and controls based on their anti-SNRPB-IgA concentrations.

Novel autoantibodies such as anti A4-Fla2, flaD, XAGE2, and CDC42EP1 were identified for IgG antibody with sensitivity of 50%, 24%, 14%, and 10% respectively at 95% specificity. We also identified novel autoantibodies for IgA antibody for anti A4-Fla2, PPP1R13L, FOSL1, SNRPB, CCHCR1, LCORL, NUPL1, PRPH, PTTG1, SNAI1, and ORC2L with sensitivity of 20%, 14%, 13%, 24%, 13%, 10%, 10%, 16%, 16%, 17%, and 10% respectively at 95% specificity.

We also assayed one special type of AAb, rheumatoid factor (RF), in CD patients and controls. All three classes of RFs, IgG, IgA and IgM, were assayed by ELISA in all 96 cases and controls. Similar to those reported in the literature, at 95% specificity, the sensitivity of the RF-IgA was 24.0%. IgM only had a sensitivity of 7.3%, while IgG had a sensitivity of 17.7%. They did show complementarity in CD patients, but their combination did not yield a better performance than that for RF-IgA alone.

Figure 5:
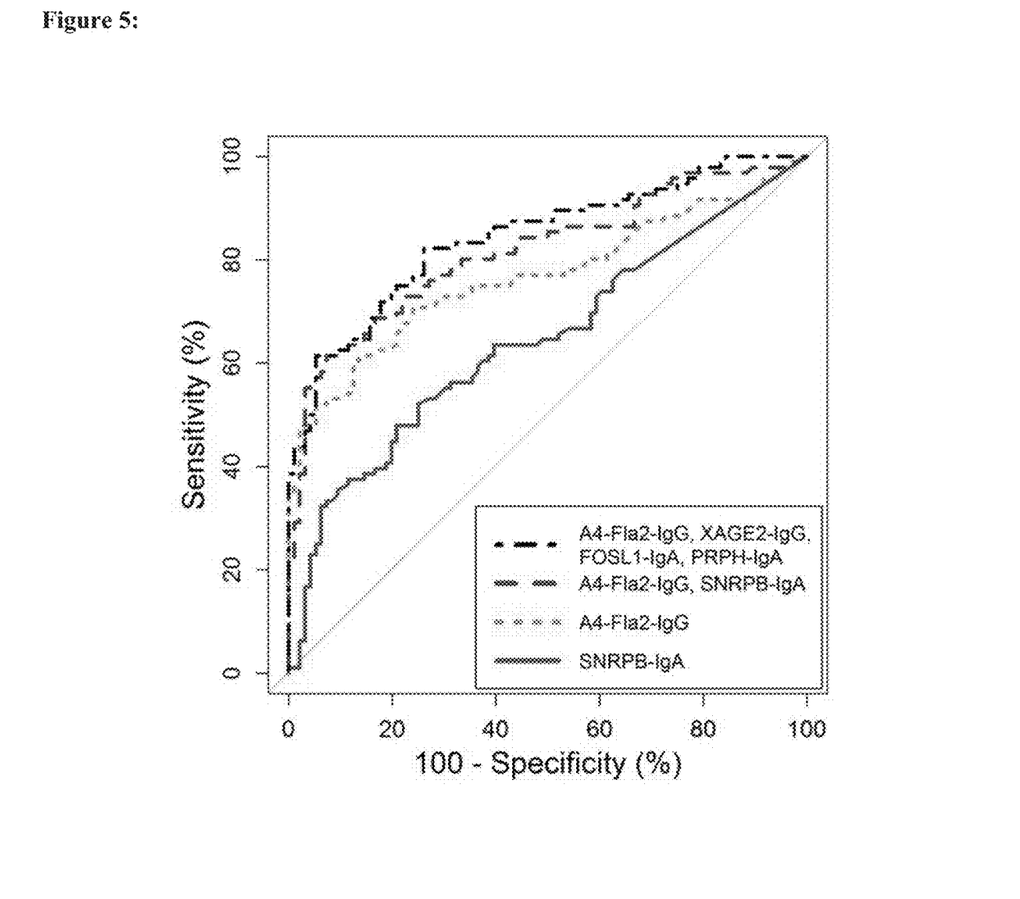
FIG. 5 shows ROC analysis of individual antibodies and antibody panels obtained from logistic regression models.
Figure 6:
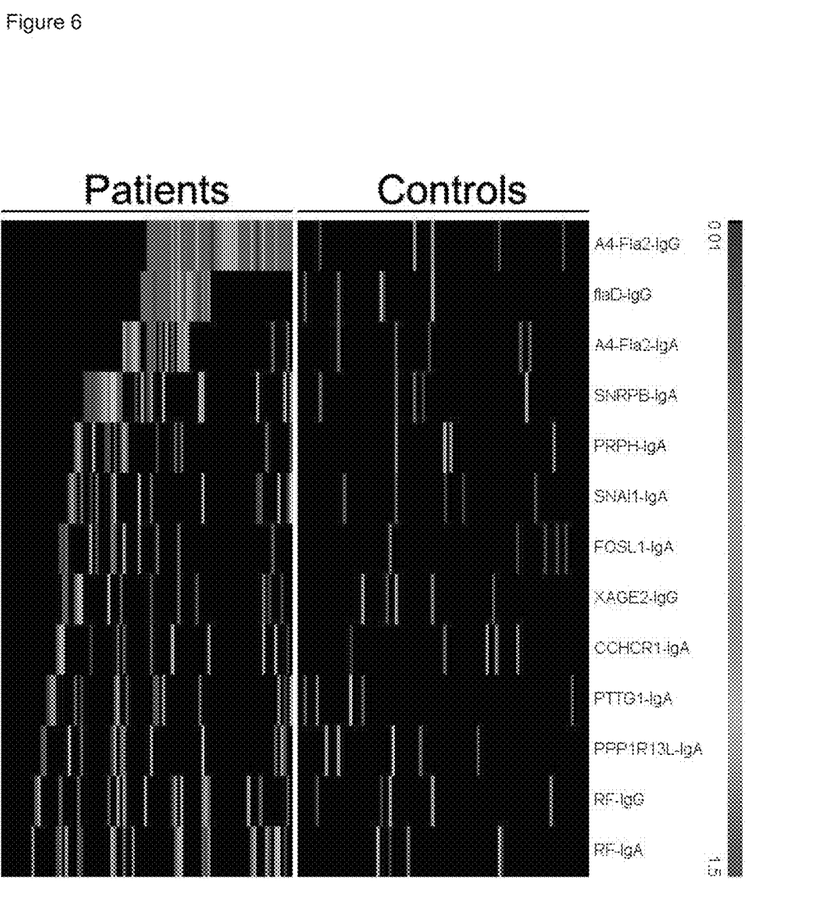
FIG. 6 is a heat map of antibody responses of novel AAbs (>10% sensitivity at 95% specificity) and RFs showing complementarity to anti-flagellin antibodies.

A receiver operating characteristic (ROC) analysis is applied to the antibodies against A4-Fla2, RF and all AAbs with a performance greater than 10% sensitivity at 95% specificity in the full sample set. Anti-A4-Fla2-IgG has the best performance in the 96 pairs of samples with 50% sensitivity at 95% specificity and an AUC of 0.767. The best novel AAb, anti-SNRPB-IgA, which is a core component of small nuclear ribonucleoprotein, provides a sensitivity of 24.0% at 95% specificity with an AUC of 0.645 (FIG. 5). The heat map (FIG. 6) showed the complementarity of the newly found antibodies and the RF to the known anti-A4-Fla2. Logistic regression was applied to these antibodies to generate panels with better performance. The logistic regression model of anti-A4-Fla2-IgG and anti-SNRPB-IgA had a sensitivity of 57.3% and increased the AUC to 0.817. The best logistic regression model included A4-Fla2-IgG, FOSL1-IgA (Fos-related antigen 1), PRPH-IgA (peripherin), and XAGE2-IgG (X antigen family member 2) and the sensitivity reached 60.4% at 95% specificity and AUC 0.844 (FIG. 4). The second best model included anti-SNRPB-IgA with a slightly higher AUC 0.852 and a slightly lower sensitivity of 59.4% at 95% specificity.

Figure 7:
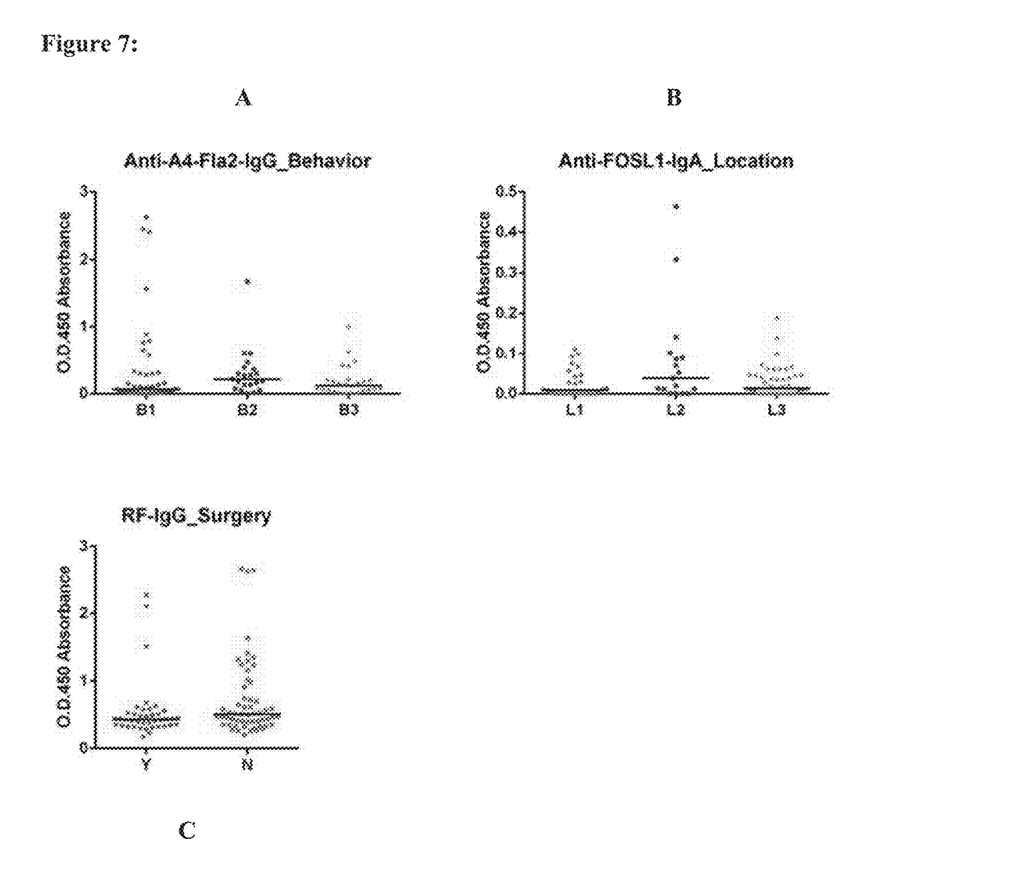

The association between different clinical parameters, including age, gender, disease behavior (B1: non-stricturing, non-penetrating; B2: stricturing; B3: penetrating) and location (L1: ileal; L2: colonic; L3: ileocolonic) based on Montreal classification, and surgery status, and antibody reactivity were also evaluated, (Table 4). None of the antibodies were significantly associated with any aspect of disease behavior. Anti-A4-Fla2 antibody has been reported to be associated with the stricturing B2 phenotype. Referring to panel A of FIG. 7, a significantly higher reactivity in B2 patients relative to B1 and B3 patients was not observed, although B2 patients did have a higher median reactivity. No significant association was observed between anti-SNRPB-IgA and patient sub-grouped by clinical parameters (data not shown). Referring to panel B of FIG. 7, anti-FOSL1-IgA was found to be significantly associated with colonic disease location (L2) (p=0.004, Table 4). RF-IgA also showed higher reactivity in patients with colonic disease (L2) relative to patients with ileal (L1) and ileocolonic (L3) diseases, but did not reach significance (p=0.086) (Table 4). Anti-PPP1R13L-IgA was negatively associated with ileal disease (p=0.03) (data not shown). Interestingly, referring to panel C of FIG. 7, patients without surgery had significantly higher RF-IgG relative to those with surgery (p=0.017). It is not clear whether the decreased RF is a consequence of the surgery and other related treatment or a sign of improvement in inflammation and healing.

TABLE 4

P-values of the hypothesis tests of association between the antibody levels and the clinical status.

| Antibody | Severity | Location | Gender | Surgery |
|---|---|---|---|---|
| A4-Fla2-IgG | 0.536 | 0.568 | 0.685 | 1.000 |
| flaD-IgG | 0.685 | 0.507 | 0.610 | 0.202 |
| A4-Fla2-IgA | 0.286 | 0.593 | 0.873 | 0.311 |
| XAGE2-IgG | 0.212 | 0.308 | 0.854 | 0.361 |
| CDC42EP1-IgG | 0.150 | 0.272 | 0.682 | 0.911 |
| PPP1R13L-IgA | 0.643 | 0.192 | 0.446 | 0.731 |
| FOSL1-IgA | 0.828 | 0.004 | 0.650 | 0.191 |
| SNRPB-IgA | 0.623 | 0.949 | 0.318 | 0.202 |
| PTTG1-IgA | 0.458 | 0.478 | 0.371 | 0.888 |
| PRPH-IgA | 0.621 | 0.217 | 0.751 | 0.471 |
| CCHCR1-IgA | 0.637 | 0.785 | 0.650 | 1.000 |
| LCORL-IgA | 0.806 | 0.540 | 0.297 | 0.587 |
| NUPL1-IgA | 0.727 | 0.349 | 0.344 | 0.417 |
| SNAI1-IgA | 0.634 | 0.849 | 0.581 | 0.346 |
| ORC2L-IgA | 0.931 | 0.394 | 0.682 | 0.587 |
| RF-IgG | 0.918 | 0.792 | 0.184 | 0.017 |
| RF-IgA | 0.737 | 0.086 | 0.170 | 0.440 |

There are two possible functional consequences of autoantibodies in CD. One is that these antibodies reflect dysregulated immune response in the gut. It is also possible that these autoantibodies could play a pathogenic role. However, the few autoantibodies discovered so far in CD limit our exploration of their functional consequences. Our establishment of a NAPPA based immunoproteomics platform should promote such discoveries.

Although the identified candidates warrants future investigation to understand the physiological relevance, they highlight the need for identifying more individual antigens in Crohn's Disease. Future studies will need to be performed on larger human proteome and CD-related microbial organism proteomes using patient samples with accurate clinical information. This work will not only yield markers that can improve our understanding of disease pathogenesis but also facilitate better management of CD patients.

Several AAbs have been reported in CD before. Anti-neutrophil cytoplasmic antibodies (ANCAs) have been found in 5-31% of patients with CD. In addition to ANCAs, other AAbs have been identified in CD, such as antibodies against the exocrine pancreas (PAb). Long after the initial observation of ANCA and PAb by immunofluorescence, the advancement of mass spectrometry technology led to the identification of CUZD1 and GP2 as two contributing AAgs for PAb from reactive western blot bands. However, few studies have applied high-throughput quantitative immuno-proteomics technologies in the study of serological markers in CD or IBD, in general. Our study used NAPPA that enabled proteome-level study of antibody responses without the need to purify individual proteins. We have previously applied NAPPA to the study of disease specific antibodies in various diseases. In this study, we applied NAPPA, an innovative protein array technology, to identify AAbs in CD. To our knowledge, this is one of the first studies that applied an immuno-proteomics approach in the identification of specific AAbs in CD.

We discovered a set of AAbs that had higher prevalence in CD cases compared to controls on arrays. We also validated 8 AAbs in an independent set of samples by ELISA. The classification performance of these AAb markers ranged from 13-24% sensitivity at 95% specificity. Anti-SNRPB-IgA had the best performance with a sensitivity of 24.0% at 95% specificity. Overall, the performances of these new antibodies were comparable to those of reported AAbs in CD. For example, anti-GP2-IgG was reported to have a sensitivity of 10.2% at 99% specificity by ELISA, and anti-GP2-IgA had a sensitivity of 3.4% at 99% specificity. Anti-FAM84A-IgG had a sensitivity of 18% at 95% specificity in CD. These novel AAbs could modestly complement the known anti-A4-Fla2-IgG flagellin antibody. This demonstrates that by using novel approaches it is possible to find new AAbs that have activities comparable to those previously identified.

Serologic markers have the potential to improve the diagnostic process for CD patients and minimize the need for invasive diagnostic procedures. The Prometheus IBD serology 7 panel includes AAb and anti-microbial antigen antibody markers and uses a sophisticated algorithm to evaluate the serologic test results. It is used clinically to aid IBD diagnosis; however, the panel lacks sensitivity and specificity, and has been shown to have a lower predictive value than routine laboratory testing in the diagnosis of IBD. Identification of novel CD-specific antibodies could improve the performance of currently available markers and expand the clinical utility spectrum of serological markers beyond diagnosis. Our study focused on AAbs, which have not been previously studied as extensively as anti-microbial antigen antibodies.

In view of the above, one point of novelty is the identification of the autoantigens against which antibodies were detected as candidates in CD (Table 3). Many of them have not been previously associated with CD.

Non-Limiting Examples

Characteristics of Plasma Samples

All samples were collected with written informed consent, and the study was approved by institutional review boards at Arizona State University and Mayo Clinic. Ninety-six (96) CD serum samples from patients within four years of diagnosis were selected from the Mayo Clinic Inflammatory Bowel Disease Biobank. Characteristics of CD patients including age, gender, Montreal Classification and surgery status are shown in Table 1. Ninety-six age- and gender-matched healthy control samples without a history of inflammatory bowel disease, celiac sprue or irritable bowel syndrome were selected from the Mayo Cancer Center/ Normal Serum Biobank at Mayo Clinic Rochester. The samples were evenly split into discovery and validation sets randomly. The discovery set was used for array profiling as an initial screening. The validation set was used for validating the candidate AAbs selected from the screening.

Nucleic Acid Programmable Protein Array Production

Open reading frames were obtained from DNASU (dnasu.org). All genes of interest were cloned in the nucleic acid-programmable protein array (NAPPA) compatible expression vectors with a C-terminal glutathione S-transferase (GST) fusion tag were obtained from the DNASU plasmid repository. Plasmid DNA was spotted on glass slides coated with aminosilane (APTS) (Thermo Fisher Scientific) in a printing buffer consisting of anti-GST polyclonal antibody (GE Healthcare), BSA and bissulfosuccinimidyl suberate protein cross-linker (Thermo Fisher Scientific, Waltham, Mass.) using a QArrayer2 (Genetix). At the time of usage, proteins were expressed from spotted plasmid DNAs using a HeLa cell lysate-based in vitro transcription and translation (IVTT) protein expression system (Thermo Fisher scientific, Rockford, Ill.). Printed arrays were blocked with the SuperBlock buffer (Thermo Fisher Scientific, Waltham, Mass.) at room temperature (RT) for 1 hr with gentle shaking. Arrays were rinsed 5 times with deionized (DI) water, dried by centrifugation at 1000 rpm for 1 minute at RT, and sealed with HybriWell (Grace BIO-LABS, Bend, Oreg.). A 155 µL human IVTT mixture was injected into the HybriWell and incubated at 30° C. for 1.5 hrs for protein expression. Expressed GST-tagged proteins were captured in situ by the anti-GST antibodies co-printed on the glass slides and displayed for subsequent serological profiling.

Serum Antibody Profiling

Expressed NAPPA arrays were washed 3 times with 5% milk-PBST (PBS with 0.2% Tween), blocked in 5% milk-PBST for 1 hr, rinsed with DI water 10 times, and dried by centrifugation at 1000 rpm for 1 min at RT. Arrays were then placed in the hybridization chambers of the HS 4800™ Pro hybridization station (Tecan, Mannedorf, Switzerland) and programmed with 5% milk-PBST wash, 16 hr incubation of 160 µL 1:20 diluted serum at 4° C., 5% milk-PBST wash, 1 hr incubation of 160 µL 1:500 diluted Alexa Fluor 647® Goat Anti-Human IgG and 1:300 diluted Cy3 Goat Anti-Human IgA (Jackson ImmunoResearch Laboratories, West Grove, Pa.) and 5% milk-PBST wash. Slides were rinsed with DI water, dried by centrifugation and scanned by a Tecan scanner under consistent settings. A pooled sample was prepared by mixing equal volumes of samples from 48 patients and 48 controls. The pooled sample was run as a technical replicate on every serum screening day.

Candidate Selection

Strong antibody reactivity sometimes resulted in saturated signals of the local spot with diffusion to the neighboring spots, which was defined as a ring. Antibody reactivity was qualitatively determined based on the existence of rings. Quantitative array image analysis was performed based on the signal intensity around the spot as published before. The reference, Bian X, Wallstrom G, Davis A, et al. Immunoproteomic profiling of antiviral antibodies in new-onset type 1 diabetes using protein arrays. *Diabetes* 2016; 65:285-96, is incorporated herein in its entirety. The raw intensity was defined as the median intensity around the spot. Spots without an evident ring were assigned zero intensity. For each candidate, the 95 percentile of the intensity of the control samples was used as the cutoff, and all the candidates were ranked by their sensitivity according to the arbitrary cutoff. Those with higher than 15% sensitivity were selected and then confirmed by ELISA using the same sample set.

ELISA Assays

Rapid Antigenic Protein in situ Display (RAPID) ELISA was performed to assess antigen specific serum antibodies as described. Ninety-six (96)-well ELISA plates (Corning Life Sciences, Salt Lake City, Utah) were coated with 50 µL 10 µg/mL anti-GST antibody (GE Healthcare, Pittsburgh, Pa.) in a coating buffer (0.5 M carbonate bicarbonate buffer, pH 9.6) overnight at 4° C. On the next day, plates were washed three times with 100 µL PBST and blocked with 100 µL 5% milk-PBST for 1.5 hrs. In the meantime, candidate antigens were expressed in the human HeLa cell lysate-based protein expression system at 30° C. for 1.5 hr from 200 ng/µL antigen encoding plasmids (pANT7-cGST), which were the same as those used to express proteins on arrays that supported the expression of proteins with a C-terminal GST tag. Expressed proteins were diluted in milk-PBST at 1:50 dilution. 50 μL diluted antigen was added into each well to allow the GST-tagged antigen to be captured by the coated anti-GST antibody at RT for 1 hr on a shaker at 500 rpm. All the wells in the plates were washed 5 times with PBST, incubated with diluted serum (1:50 to 1:200 serum dilution for human protein and 1:500 to 1:10000 for bacterial protein) at RT for 1 hr, washed 5 times with PBST, and incubated with 50 μL 1:10,000 diluted HRP labeled Goat Anti-Human IgG or Goat Anti-Human IgA (Jackson ImmunoResearch Laboratories, West Grove, Pa.) at RT for 1 hr on a shaker at 500 rpm. Finally, plates were washed and incubated with 1-Step Ultra TMB-ELISA Substrate (Thermo Fisher scientific, Waltham, Mass.) for 10 min for detection and 50 μL 2M sulfuric acid was added to stop the reaction. O.D.450 was measured immediately by Envision® Multilabel Reader (PerkinElmer, Waltham, Mass.).

Plates coated with 50 μL 50 μg/mL goat IgG antibody (Jackson ImmunoResearch Laboratories, West Grove, Pa.) were used to assess rheumatoid factor (RF). After incubating with serum samples, plates were incubated with 1:10,000 diluted HRP labeled Goat-Anti-Human IgG, or IgA, or IgM to probe different classes of RF.

Plates coated with serially diluted human IgA (Jackson ImmunoResearch Laboratories, West Grove, Pa.) ranging from 0 to 1 μg/ml were used to generate a standard curve for IgA ELISA. A four parameter logistic equation was used to fit the curve. Serum concentrations of anti-SNRPB-IgA antibody in μg/mL were estimated based on the standard curve using the O.D.450 absorbance data.

Statistics and Data Analysis

The overall qualitative reactivity between cases and controls based on the array data was compared using descriptive statistics and one-tailed Student's t-test assuming equal variance with null hypothesis that cases have stronger antibody reactivity. The performance of the individual candidates and combined classifiers were assessed by ROC analysis. For the panel construction, the bestglm package in R was used to select logistic regression model based on Akaike information criterion (AIC) while only individual candidates with higher than 10% sensitivity at 95% specificity in the entire sample set were included. For the subtype analysis, two-tailed Student's t-test assuming unequal variance was used to exam the association between the antibody responses against different antigens and clinical information including gender and surgery status. One-way ANOVA was used for the association between the antibody responses against different antigens and non-binomial clinical information such as behavior and disease location. Student's t-test and Mann-Whitney U test were used to test the differences between patient subgroups. The heat map was generated in MultiExperiment based on the ELISA data. Graphs and plots were drawn in GraphPad or in R.

Identification of Candidate Antigens Associated with Crohn's Disease

To identify CD-associated candidate Abs, we first performed comprehensive profiling of antibodies against 1906 unique human proteins in serum samples from forty-eight (48) CD patients and 48 age-gender matched healthy controls on NAPPA arrays. Based on array data, we selected the following antigens A4-Fla2, flaD, XAGE2, and CDC42EP1 for IgG antibody and for IgA antibody anti A4-Fla2, PPP1R13L, FOSL1, SNRPB, CCHCR1, LCORL, NUPL1, PRPH, PTTG1, SNAI1, and ORC2L that showed high antibody reactivity on the NAPPA arrays (Table 3). Antibodies against SNRPB-IgA had the best performance with a sensitivity of 24.0% at 95% specificity.

Validation of Candidate Antigens Associated with Crohn's Disease

To validate these novel antibodies, we performed a validation study of responses in ELISA to A4-Fla2, flaD, XAGE2, and CDC42EP1 for IgG antibody and for IgA antibody anti A4-Fla2, PPP1R13L, FOSL1, SNRPB, CCHCR1, LCORL, NUPL1, PRPH, PTTG1, SNAI1, and ORC2L in an independent set of 96 serum samples from groups of subjects with two different clinical characteristics: CD patients (48) and healthy controls (48) (Table 1). We observed significant differences for the antigens' reactivity between the CD patients and healthy control groups (Table 3, FIGS. 2, 4, and 5).

Using an immuno-proteomics approach, we applied serum samples to arrays displaying thousands of proteins in parallel. We discovered a set of AAbs that had higher prevalence in CD cases compared to controls on arrays. We also validated 8 AAbs in an independent set of samples by ELISA. The classification performance of these AAb markers ranged from 13-24% sensitivity at 95% specificity.

Serologic markers have the potential to improve the diagnostic process for CD patients and minimize the need for invasive diagnostic procedures. The Prometheus IBD serology 7 panel includes AAb and anti-microbial antigen antibody markers and uses a sophisticated algorithm to evaluate the serologic test results. It is used clinically to aid IBD diagnosis; however, the panel lacks sensitivity and specificity, and has been shown to have a lower predictive value than routine laboratory testing in the diagnosis of IBD. Identification of novel CD-specific antibodies could improve the performance of currently available markers and expand the clinical utility spectrum of serological markers beyond diagnosis. Our study focused on AAbs, which have not been previously studied as extensively as anti-microbial antigen antibodies.

Naturally folded protein arrays like NAPPA aid in the discovery of antibodies against human proteins in CD. We profiled fewer than 2000 human proteins in this study, which represents a small fraction of human proteins and microbial proteins in our collections. The success of this study suggests excellent outcomes for future expanded studies. Furthermore, we can produce protein arrays with any cDNA sequences at a low cost. This flexibility of NAPPA combined with next gen sequencing technologies make it uniquely possible to study antibody responses to antigens encoded CD related microorganisms as they are discovered by microbiome studies in the future. It is believed that no single antigen will meet all clinical needs. Achieving the best performance will rely on a panel of antibodies. An immunoproteomics approach using protein arrays will facilitate the discovery of additional antibodies, creating the opportunity to combine them into panels that can benefit the clinical management of CD patients. Our data supported this assumption.

SNRPB is the core component of spliceosomal small nuclear ribonucleoproteins (snRNPS) and plays an important role in pre-mRNA splicing. SNRPB is an AAg in Systemic Lupus Erythematous (SLE) patients originally identified as the 'smith antigen' (Sm). Whereas reactivity to this antigen in SLE is primarily of the IgG subtype, we observed that in CD it is primarily IgA. It would be of great interest to assay anti-SNRPB-IgA and anti-SNRPB-IgG in SLE and CD patients to further confirm antibody subtype specificity in these two diseases.

There are two possible functional consequences of autoantibodies in CD. One is that these antibodies reflect dysregulated immune response in the gut. It is also possible that these autoantibodies could play a pathogenic role. However, the few autoantibodies discovered so far in CD limit our exploration of their functional consequences. Our establishment of a NAPPA based immunoproteomics platform should promote such discoveries. In the case of the novel autoantibodies reported in our study, future validation and association studies with clinical parameters in a larger sample set, assays of their titer changes over time during CD development, and their expression patterns in the gut, should shed light on their role of autoimmunity.

We also calculated the sensitivities and specificities of all candidate antigens that went into the validation study. In summary, we have demonstrated that serological profiling on NAPPA in the discovery of AAbs in CD has great potential. Future studies will need to be performed on larger human proteome and CD-related microbial organism proteomes using patient samples with accurate clinical information. This work will not only yield markers that can improve our understanding of disease pathogenesis but also facilitate better management of CD patients.

Although we had clinical information available on disease phenotype, duration and prior surgeries, the serum samples were procured at different stages of the patients' diseases, and not necessarily at the time of high disease activity or surgery. Second, several patients were receiving medical therapy with different agents, including steroids, immunomodulators and/or biologics, while some patients were not on maintenance therapy. All these confounding factors might have contributed to relatively weak signals for the association analysis. Third, our study focused on AAbs that can differentiate CD patients from healthy subjects and we did not study patients with ulcerative colitis. In the future, we need to assess the CD specificity of the antibodies we discovered against UC patients in addition to the healthy controls we have assessed. Fourth, we note that proteins on the arrays may lack some native post-translational modifications (PTMs) that might be important for some antibody-antigen interactions.

In summary, we have developed a platform that can assay sero-reactivity to many CD related proteins in parallel. We screened 1906 proteins, to determine reactivity in CD sera to known and novel proteins. We observed unique antibody reactivity patterns. At individual antigen levels, antibodies against A4-Fla2, flaD, XAGE2, and CDC42EP1 were identified for IgG antibody and for IgA antibody anti A4-Fla2, PPP1R13L, FOSL1, SNRPB, CCHCR1, LCORL, NUPL1, PRPH, PTTG1, SNAI1, and ORC2L.

While the preferred embodiments of the present technology have been illustrated in detail, it should be apparent that modifications and adaptations to those embodiments may occur to one skilled in the art without departing from the scope of the present technology.

What is claimed is:

1. A method for detecting an autoantibody of Crohn's disease in a subject comprising: disposing a plurality of DNA segments corresponding to different open reading frames of genes on an array, wherein each DNA segment comprises a nucleic acid sequence encoding a fusion tag; disposing a plurality of antibodies raised against the fusion tag on the array; translating the plurality of DNA segments to a plurality of polypeptides, wherein each polypeptide comprises the fusion tag and is captured by the antibodies raised against the fusion tag, wherein the plurality of captured polypeptides are selected from the group consisting of A4-Fla2, flaD, XAGE2, CDC42EP1, PPP1R13L, FOSL1, SNRPB, CCHCR1, LCORL, NUPL1, PRPH, PTTG1, SNAI1 and ORC2L, and incubating the array comprising the plurality of captured polypeptides with a sample collected from a subject suspecting having the disease, identifying the subject having Crohn's disease based, at least in part, on the presence of the polypeptide/autoantibody complex; and administering a medical therapy selected from the group consisting of therapeutic steroids, immunomodulators, and biologics.

2. The method of claim 1, wherein the disposing a plurality of DNA segments step further comprises coating the array with aminosilane.

3. The method of claim 1, wherein the fusion tag is a C-terminal glutathione S-transferase (GST) fusion tag.

4. The method of claim 1, wherein the disposing a plurality of antibodies step further comprises incubating the array in a printing buffer containing anti-GST polyclonal antibodies.

5. The method of claim 1, wherein the translating step further comprises expressing polypeptides from the disposed plurality of DNA segments using a HeLa cell lysate-based in vitro transcription and translation (IVTT) protein expression system.

6. The method of claim 5, wherein the expressing step further comprises incubating the array with a human IVTT mixture.

7. The method of claim 1, wherein the plurality of captured polypeptides comprise A4-Fla2, FOSL1, PRPH, and XAGE2.

8. The method of claim 1, wherein the plurality of captured polypeptides comprise A4-Fla2, FOSL1, PRPH, XAGE2, and SNRPB.

9. The method of claim 1, wherein the plurality of captured polypeptides comprise A4-Fla2 and SNRPB.

10. The method of claim 1, wherein the plurality of captured polypeptides comprise SNRPB.

11. The method of claim 1, wherein the plurality of DNA segments corresponding to different open reading frames of genes are obtained from DNASU plasmid repository.

12. The method of claim 1, wherein the plurality of DNA segments corresponding to different open reading frames of genes encode about 1900 different human proteins.

13. The method of claim 1, wherein the sample is a blood or serum sample.

14. The method of claim 1, wherein the disease is Crohn's disease.

* * * * *

UNITED STATES PATENT AND TRADEMARK OFFICE
CERTIFICATE OF CORRECTION

| | |
|---|---|
| PATENT NO. | : 10,648,978 B2 |
| APPLICATION NO. | : 15/892981 |
| DATED | : May 12, 2020 |
| INVENTOR(S) | : Haoyu Wang et al. |

It is certified that error appears in the above-identified patent and that said Letters Patent is hereby corrected as shown below:

In the Claims

Column 14, Line 11, Claim 1, delete "SNAII" and insert -- SNAI1, --, therefor.

Signed and Sealed this
Seventh Day of June, 2022

*Katherine Kelly Vidal*

Katherine Kelly Vidal
*Director of the United States Patent and Trademark Office*